United States Patent [19]

Grollier

[11] Patent Number: 4,834,969
[45] Date of Patent: May 30, 1989

[54] ORAL CARE COMPOSITION IN THE FORM OF AEROSOL FOAM

[75] Inventor: Jean F. Grollier, Paris, France

[73] Assignee: L'Oreal, Paris, France

[21] Appl. No.: 51,130

[22] Filed: May 18, 1987

[30] Foreign Application Priority Data

May 21, 1986 [LU] Luxembourg ............................ 86433

[51] Int. Cl.$^4$ .......................... A61K 7/16; A61K 9/12
[52] U.S. Cl. ........................................ 424/49; 424/45
[58] Field of Search ..................... 424/45, 49

[56] References Cited

U.S. PATENT DOCUMENTS

| | | | |
|---|---|---|---|
| 3,914,406 | 10/1975 | Yankell | 424/52 |
| 3,947,566 | 3/1976 | Sarna et al. | 424/45 |
| 3,947,567 | 3/1976 | Berg et al. | 424/45 |
| 3,947,568 | 3/1976 | Bates et al. | 424/45 |
| 3,972,996 | 8/1976 | Pitts et al. | 424/49 |
| 4,214,006 | 7/1980 | Thiele | 514/560 |

FOREIGN PATENT DOCUMENTS

| | | | |
|---|---|---|---|
| 1465495 | 2/1977 | United Kingdom . | |
| 2140691A | 5/1984 | United Kingdom . | |
| 2140691 | 12/1984 | United Kingdom | 424/49 |

*Primary Examiner*—Shep K. Rose
*Attorney, Agent, or Firm*—Marshall, O'Toole, Gerstein, Murray & Bicknell

[57] ABSTRACT

Composition intended for cleaning, disinfecting and deodorizing the buccal cavity and teeth characterized in that it contains, in an aqueous medium, at least one nonionic surfactant of the poly(hydroxypropylether) group, that it is packaged in a pressurized aerosol device in the presence of a propellant chosen from among partially halogenated hydrocarbons so as to form a short-lived foam on dispensing from the pressurized device.

10 Claims, No Drawings

ORAL CARE COMPOSITION IN THE FORM OF AEROSOL FOAM

The subject of the present invention is a composition for cleaning, disinfecting and/or deodorizing the buccal cavity and teeth, in the form of an aqueous aerosol foam with a short life on contact with the buccal mucus or with teeth.

The use of compositions for washing and mouth, also called mouthwashes, dispensed in the form of a foam from an aerosol packaging with a view to cleaning, disinfecting and/or deodorizing the mouth and the teeth has already been proposed. Such compositions are especially intended for removing food desposits and to act in the prevention of tartar, caries and bad odours of the mouth. Such products are described especially in Japanese Pat. Nos. 55/085,513, 57/014,520, 57/014,521 and in German patent application No. 2,001,317.

However, the compositions in the prior art most frequently give rise to firm and rich foams with relatively long staying power and which are relatively large in volume. With this object in view, they contain essentially anionic surfactants such as sodium lauryl sulphate, sodium dodecyl benzenesulphonate, a sodium salt of lauryl sarcosinate and, in some cases, surfactants which enable the texture of the foam to be further improved, such as lauryl diethanolamide. These compositions are generally in the form of a paste which additionally contains an abrasive polishing agent and are used in the form of a toothpaste, using a brush. When they are intended to be used in the form of mouthwashes, it is recommended to deposit the foam beforehand in a mouthwashing cup and to dilute it to several times its volume with water, stirring it well to make it dissolve. Such a composition cannot therefore be used directly for washing the mouth.

Moreover, the availability of a composition which cleans, disinfects and deodorizes the entire buccal cavity and which can be used easily at any time without the need to use accessories or to dissolve the product has been sought.

The Applicant has discovered that direct treatment with a foam instead of a liquid composition was much more efficient in cleaning, disinfecting and deodorizing the mouth. This appears to be due to the more efficient wetting qualities of the compositions in the form of a foam, with a better distribution and a better penetration into the interstices between the teeth and a more efficient removal of the food debris and a better deodorization, although this explanation should not be regarded as limiting.

The Applicant has therefore sought to obtain a composition which has the advantages mentioned above, i.e. which makes it possible to clean, disinfect and deodorize by dispensing it directly into the mouth from an aerosol packaging. However, such a foam must break up after impregnating the mucus or the teeth in a sufficiently short period of time so that it can be discarded in the liquid form. This type of foam will be called "short lived foam" or, in the Anglo-Saxon terminology, "quick breaking" foam. A foam for the direct treatment of the buccal cavity and the teeth is considered short-lived when it disappears, i.e. it becomes liquefied, in a period of less than 25 seconds after its formation.

This disappearance time for the foam may be determined, for example, according to the following test:

1 g of the foam according to the invention is deposited on a watch glass and the time required for it to become liquefied is measured with a timer; 1 g of foam becomes liquefied within approximately 20 seconds. The quantity by weight of foam which can temporarily be deposited in the buccal cavity and on teeth has been determined separately. This quantity may vary from 0.3 to 1 g, preferably 0.4 to 0.6 g and disappears on contact with mucuses and with teeth, in periods varying between 10 and 15 seconds.

The surfactants recommended until now in the prior art and the propellents used in combination with these surfactants do not enable buccal foams which are short-lived and non-attacking towards mucuses to be obtained.

The Applicant has discovered that it was possible to prepare a short-lived buccal foam which can be used directly on the buccal mucus and the teeth without the need for it to be dissolved, by using at least one nonionic surfactant of the poly(hydroxypropylether) group as the surfactant and a partially halogenated hydrocarbon as the propellant.

The subject of the invention is therefore a composition based on nonionic surfactants of the poly(hydroxypropylether) group, pressurized in an aerosol device in the presence of a propellant chosen from amongst partially halogenated hydrocarbons.

Another subject of the invention consists of a method for washing the buccal cavity or teeth, using this composition dispensed in the form of a foam.

Other subjects of the invention will become apparent on reading the description and the examples which follow.

The oral care composition according to the invention is essentially characterized in that it consists of an aqueous or aqueous/alcoholic solution containing at least one nonionic surfactant from the poly(hydroxypropylether) group, packaged in a pressurized device in the presence of a propellant chosen from amongst partially halogenated hydrocarbons.

The nonionic surfactants of the poly(hydroxypropylether) group used according to the invention are more particularly chosen from amongst compounds which correspond to the formulae (I), (II) and (III) below or from amongst compounds prepared according to the process described in paragraph (iv) below

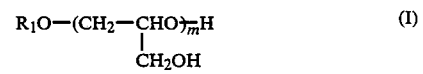

in which $R_1$ denotes an alkyl group or a mixture of alkyl groups containing 10 to 14 carbon atoms and m is an integer or real number from 2 to 10 and preferably from 3 to 6;

in which $R_2$ denotes an alkyl group or a mixture of alkyl groups containing 8 to 12 carbon atoms and n denotes an integer or a real number from 2 to 10 and preferably from 2.5 to 6;

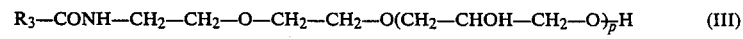

in which $R_3$ denotes an alkyl or alkenyl radical or a mixture of alkyl and/or alkenyl radicals containing from 11 to 17 carbon atoms and p denotes an integer or a real number from 1 to 5 and preferably from 1.5 to 4.

(iv) Compounds prepared by acid-catalyzed condensation of 2 to 10 and preferably 2.5 to 6 moles of glycidol per mole of alcohol or of alcane-1,2-diol containing 10 to 14 carbon atoms as described especially in French Pat. No. 2,169,787.

The surfactants which are particularly preferred in the compositions according to the invention correspond to the formulae:

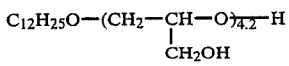  (IV)

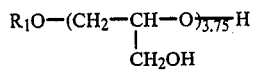  (V)

in which $R_1$ denotes a mixture of $C_{10}H_{21}$ and $C_{12}H_{25}$ alkyl radicals;

  (VI)

in which $R_2$ denotes a mixture of $C_9H_{19}$ to $C_{12}H_{25}$ alkyl radicals;

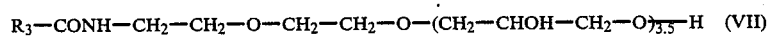  (VII)

in which $R_3$ denotes a mixture of groups comprisig $C_{12}H_{25}$ and $C_{14}H_{29}$ alkyl groups, alkyl and alkenyl radicals derived from coconut oil fatty acids or an oleyl group; and

  (VIII)

The more particularly preferred surfactants are those corresponding to formula (VI) above.

The abovementioned surfactants are used in the oral care compositions according to the invention at concentrations of between 0.2 and 3% by weight, preferably between 0.5 and 2% by weight relative to the total weight of the composition.

The propellents used in the pressurized aerosol device are chosen from amongst partially halogenated hydrocarbons. A particularly preferred propellant consists of a chlorodifluoromethane such as the product sold by Du Pont De Nemours under the mane "Dymel 22" which is also call "Freon 22" or of a difluoroethane such as the product sold by Du Pont De Nemours under the name Dymel which is also called "Freon 152 A". The propellant is present in the pressurized device in proportions of the order of 5 to 20% by weight relative to the total weight of the composition and preferably 8 to 12%.

In addition to the nonionic surfactants of the poly(hydroxypropylether) group, the compositions according to the invention may contain other surfactants and more particularly surfactants which have bactericidal properties intended especially to prevent the formation of dental plaque. These are generally cationic nitrogenous compounds amongst which may be mentioned: benzyldimethyl ($C_8$-$C_{18}$ alkyl)ammonium chloride; diisobutyl phenoxyethoxyethyldimethylbenzylammonium chloride; dodecyl trimethylammonium bromide; dodecyl dimethyl-(2-phenoxyethyl) ammonium bromide; benzyldimethylstearylammonium chloride; cetylpyridinium chloride; quaternised 5-amino-1,3-bis(2-ethylhexyl)-5-methylhexahydroxypyrimidine; trimethylcetyl ammonium bromide; alkyldimethylhydroxyethylammonium bromide in which the alkyl group is a mixture of radicals derived from coconut oil fatty acids; chlorhexidine; alexidine and long chain tertiary amines.

These bactericidal agents are generally used in proportions of 0.005 to 10% by weight and preferably 0.05 to 2% by weight relative to the total weight of the composition.

These compositions may also contain thickeners such as, more particularly, natural gums or synthetic thickeners among which sodium alginate, carragheen gum, xanthan gum, and sodium salt of carboxymethylcellulose and hydroxyalkylcelluloses may be mentioned.

These thickeners must be present in buccal compositions in proportions which always enable short-lived foam to be obtained and generally in proportions less than or equal to 0.5% and preferably less than or equal to 0.25%.

The short-lived buccal foams according to the invention generally contain a sweetening agent at concentrations which may range between 5 and 30%, preferably between 10 and 20% relative to the total weight of the composition. Among these agents, sorbitol, glycerine and sodium saccharinate may be mentioned by way of example. They may also contain preservatives such as formol and its derivatives, methyl para-hydroxybenzoate, propyl para-hydroxybenzoate and the like in quantities of between 0.01 and 0.5% by weight relative to the total weight of the composition.

With a view to using them as mouthwashes, they generally contain a flavouring substance in proportions of preferably between 0.5 and 5% relative to the total weight of the foam expelled from the aerosol device. Oils of mint (curly mint or peppermint), aniseed, eucalyptus, cinnamon, clove, sage and liquorice and fruit essences such as oils of lemon, orange, mandarin and strawberry or possibly methyl salicylate may be mentioned for this purpose.

The compositions according to the invention are generally aqueous, but may also be present in the aqueous/ alcoholic form and may contain, in this variant, lower alkanols such as, for example, ethanol or glycols such as propylene glyco, these alcohols being present in sufficient proportions so as not to prevent foam formation. These proportions are generally less than 20% relative to the total weight of the composition.

The pH of the compositions according to the invention are generally bewteen 3 and 9 and preferably between 5 and 7.5.

The compositions according to the invention may naturally contain any other adjuvant commonly used in oral care compositions.

The invention also relates to the process for the preparation of a short-lived buccal foam by pressurizing in an aerosol device, the aqueous composition defined above, containing the poly(hydroxypropylether) surfactant, with a propellant chosen from amongst partially halogenated hydrocarbons and especially difluoroethane.

The method for cleaning, washing or disinfecting the buccal cavity, according to the invention, is essentially characterized in that a foam is dispensed from an aerosol device containing the composition defined above, in the presence of a propellant consisting of a partially halogenated hydrocarbon, into the buccal cavity or onto the teeth, this composition is maintained for a period sufficient to clean the mouth and the teeth until the foam becomes liquid and it is discarded in the liquid form.

The following examples are intended to illustrate the invention without, however, being limiting in nature.

EXAMPLE 1

The following oral hygiene composition in the form of a foam is prepared:

$$R-CHOH-CH_2-O+CH_2-CHOH-CH_2-O)_{3.5}-H$$

in which R denotes a mixture of alkyl radicals containing:

| | |
|---|---|
| 9 to 12 carbon atoms | 1 g |
| sodium saccharinate | 0.1 g |
| 70% sorbitol | 14 g AS |
| monosodium phosphate | 0.01 g |
| preservative, colorant and flavour qs | |
| water qs | 100 g |

90 g of this composition and then 10 g of difluoroethane are introduced into an aerosol container equipped with a directing nozzle. A short-lived buccal foam which dissipates in about 10 seconds on contact with buccal mucus and teeth is obtained by actuating the valve. The foam imparts a pleasant breath to the mouth and helps to loosen tartar.

EXAMPLE 2

The following oral hygiene composition in the form of a foam is prepared:

| | |
|---|---|
| non ionic surfactant of formula: R—CHOH—CH$_2$—O(CH$_2$—CHOH—CH$_2$—O)$_{3.5}$—H in which R denotes a mixture of alkyl radicals containing 2 to 12 carbon atoms | 1 g |
| sodium saccharinate | 0.13 g |
| 70% sorbitol | 14 g MA |
| chlorhexidinedigluconate | 0.05 g |
| monosodium phosphate | 0.2 g |
| Preservative, colorant. flavour qs | |
| Water qs | 100 g |

90 g of this composition and 10 g of chlorodifluoromethane are introduced into an aerosol container equipped a directing nozzle.

A short-lived buccal foam which dissipates in about 10 seconds on contact with buccal mucus and teeth is obtained by actuating the valve.

EXAMPLES 3, 4, 5, 6
The following oral hygiene compositions in the form of a foam are prepared:

| | Ex 3 | Ex 4 | Ex 5 | Ex 6 |
|---|---|---|---|---|
| non ionic surfactant of formula: C$_{12}$H$_{25}$O—(CH$_2$—CH—O)$_{4.2}$—H<br>                                                      CH$_2$OH | 1 g | | | |
| non ionic surfactant of formula R—CONH—(CH$_2$)$_2$—O—(CH$_2$)$_2$—O—(CH$_2$—CHOH—CH$_2$—O)$_{3.5}$—H In which R denotes the following mixture of alkyl/or alkenyl radicals 35% C$_{12}$H$_{25}$ —15% C$_{14}$H$_{29}$ —15% oleyl radicals 35% copran fatty acids radicals | | 1 g | | |
| non ionic surfactant of formula: C$_{10}$H$_{21}$—CHOH—CH$_2$—O (CH$_2$—CHOH—CH$_2$—O)$_{2.5}$—H | | | 1 g | 0.3 g |
| Sodium saccharinate (g) | 0.13 | 0.13 | 0.13 | 0.13 |
| 70% sorbitol (g Ma) | 14 | 14 | 14 | 14 |
| Monosodium phosphate (g) | 0.2 | 0.2 | 0.2 | 0.2 |
| cetyl pyridynium chloride (g) | | 0.8 | | |
| Preservative, flavour, colorant qs | | | | |
| Water qs (g) | 100 | 100 | 100 | 100 |

The compositions are packaged according to the procedure of example 1 with the difluoroethane and short-lived foams which dissipate in about 10 seconds on contact with buccal mucus and teeth are delivered by actuating the valve.

The same pressurized compositions with the chlorodifluoromethane also provide short-lived foams dissipating in the same time.

I claim:

1. Composition intended for cleaning, disinfecting and deodorizing the buccal cavity and teeth containing in an aqueous medium between 0.2 and 3% by weight of, at least one nonionic surfactant of the poly(hydroxypropylether) group, that is packaged in a pressurized aerosol device in the presence of 5 to 20% by weight of a propellant chosen from amongst partially halogenated hydrocarbons so as to form a short-lived foam liquifying in less than 25 seconds, after being dispensed from a pressurized device.

2. Composition according to claim 1, wherein the nonionic surfactant of the poly(hydroxypropylether) group is a compound of formula:

$$(i)\ R_1O-(CH_2-CHO)_{\overline{m}}H \atop\phantom{xxxxxxxxx}|\phantom{xxx}\atop\phantom{xxxxxxx}CH_2OH \qquad (I)$$

in which R$_1$ denotes an alkyl group or a mixture of alkyl groups containing 10 to 14 carbon atoms and m is an integer or real number from 2 to 10;

$$(ii)\ R_2-CHOH-CH_2O-(CH_2-CHOH-CH_2O)_{\overline{n}}H \qquad (II)$$

in which R$_2$ denotes an alkyl group or a mixture of alkyl groups containing 8 to 12 carbon atoms and n denotes an integer or a real number from 2 to 10;

(iii) $R_3-CONH-CH_2-CH_2-O-CH_2-CH_2-O(CH_2-CHOH-CH_2-O)_{\overline{p}}H$ (III)

in which $R_3$ denotes an alkyl or alkenyl radical or a mixture of alkyl and/or alkenyl radicals containing from 11 to 17 carbon atoms and p denotes an integer or a real number from 1 to 5.

(iv) Compounds prepared by acid-catalyzed condensation of 2 to 10 moles of glycidol per mole of alcohol or of alcane-1,2-diol containing 10 to 14 carbon atoms.

3. Composition according to claim 2, wherein the nonionic surfactant is a compound of formula:

$$C_{12}H_{25}O-(CH_2-\underset{CH_2OH}{\underset{|}{CH}}-O)_{\overline{4.2}}H \quad (IV)$$

$$R_1O-(CH_2-\underset{CH_2OH}{\underset{|}{CH}}-O)_{\overline{3.75}}H \quad (V)$$

in which $R_1$ denotes a mixture of $C_{10}H_{21}$ and $C_{12}H_{25}$ alkyl groups;

$$R_2-CHOH-CH_2O-(CH_2-CHOH-CH_2O)_{\overline{3.5}}H \quad (VI)$$

in which $R_2$ denotes a mixture of $C_9H_{19}$ to $C_{12}H_{25}$ alkyl radicals;

$$R_3-CONH-CH_2-CH_2-O-CH_2-CH_2-O-(CH_2-CHOH-CH_2-O)_{\overline{3.5}}H \quad (VII)$$

in which $R_3$ denotes a mixture of radicals comprising $C_{12}H_{25}$ and $C_{14}H_{29}$ alkyl radicals, alkyl and alkenyl radicals derived from coconut oil-fatty acids and an oleyl group; and $$C_{10}H_{21}-CHOH-CH_2O-(CH_2-CHOH-CH_2-O)_{\overline{2.5}}-H \quad (VIII)$$

4. Composition according to claim 1, wherein the nonionic surfactant is present in concentrations of between 0.2 and 3% by weight relative to the total weight of the composition.

5. Composition according to claim 1, wherein the propellant is difluoroethane or chlorodifluoromethane.

6. Composition according to claim 1, wherein the propellant is present in proportions of 5 to 20% relative to the total weight of the composition.

7. Composition according to claim 1, containing additionally cationic nitrogenous bactericidal agents.

8. Composition according to claim 1, further containing thickeners in proportions effective to obtain short-lived foam, ranging up to 0.5%.

9. Composition according to claim 1, containing additionally sweetening agents, preservatives, flavouring agents or mixture thereof.

10. Composition according to claim 1, wherein the aqueous medium consists of water or of a water/alcohol mixture.

* * * * *